(12) United States Patent
Moffat et al.

(10) Patent No.: US 11,382,902 B2
(45) Date of Patent: Jul. 12, 2022

(54) TREATMENT OF CANCER BY STIMULATION OF IL-12 PRODUCTION

(71) Applicant: Macrophage Pharma Limited, Hertfordshire (GB)

(72) Inventors: David Festus Charles Moffat, Windsor Berkshire (GB); Martin John Perry, Windsor Berkshire (GB); Stephen Mark Anderton, Edinburgh Lothian (GB); Clare Louise Doris, Edinburgh Lothian (GB)

(73) Assignee: MACROPHAGE PHARMA LIMITED

( * ) Notice: Subject to any disclaimer, the term of this patent is extended or adjusted under 35 U.S.C. 154(b) by 108 days.

(21) Appl. No.: 16/638,406

(22) PCT Filed: Aug. 30, 2018

(86) PCT No.: PCT/GB2018/052448
§ 371 (c)(1),
(2) Date: Feb. 11, 2020

(87) PCT Pub. No.: WO2019/043389
PCT Pub. Date: Mar. 7, 2019

(65) Prior Publication Data
US 2020/0360359 A1    Nov. 19, 2020

(30) Foreign Application Priority Data
Aug. 31, 2017   (GB) .................................. 1713975

(51) Int. Cl.
*A61K 31/4412* (2006.01)
*A61P 35/00* (2006.01)

(52) U.S. Cl.
CPC .......... *A61K 31/4412* (2013.01); *A61P 35/00* (2018.01)

(58) Field of Classification Search
CPC ............................ A61K 31/4412; A61P 35/00
See application file for complete search history.

(56) References Cited

U.S. PATENT DOCUMENTS

| 7,932,246 B2 | 4/2011 | Moffat et al. |
| 7,939,666 B2 | 5/2011 | Davidson et al. |
| 7,973,181 B2 | 7/2011 | Davidson et al. |
| 8,003,695 B2 | 8/2011 | Moffat et al. |
| 8,030,317 B2 | 10/2011 | Dong et al. |
| 8,044,211 B2 | 10/2011 | Moffat et al. |
| 8,106,091 B2 | 1/2012 | Moffat et al. |
| 8,148,531 B2 | 4/2012 | Davidson et al. |
| 8,211,900 B2 | 7/2012 | Davidson |
| 8,637,547 B2 | 1/2014 | Davidson et al. |
| 8,686,032 B2 | 4/2014 | Davidson et al. |
| 8,778,953 B2 | 7/2014 | Moffat et al. |
| 9,388,136 B2 | 7/2016 | Pintat et al. |
| 2009/0203711 A1 | 8/2009 | Moffat |
| 2009/0215800 A1 | 8/2009 | Davidson et al. |
| 2010/0004250 A1 | 1/2010 | Philips et al. |
| 2010/0010057 A1 | 1/2010 | Moffat et al. |
| 2010/0216802 A1 | 8/2010 | Moffat et al. |
| 2010/0267774 A1 | 10/2010 | Moffat et al. |
| 2010/0317678 A1 | 12/2010 | Moffat et al. |
| 2010/0317865 A1 | 12/2010 | Davidson et al. |
| 2011/0039920 A1 | 2/2011 | Moffat et al. |
| 2011/0046210 A1 | 2/2011 | Moffat et al. |
| 2011/0190306 A1 | 8/2011 | Moffat et al. |
| 2012/0035251 A1 | 2/2012 | Drummond et al. |
| 2012/0149736 A1 | 6/2012 | Donald et al. |
| 2013/0143926 A1 | 6/2013 | Donald et al. |
| 2013/0197042 A1 | 8/2013 | Davidson et al. |
| 2013/0303576 A1 | 11/2013 | Donald et al. |
| 2014/0010762 A1 | 1/2014 | Charlton et al. |
| 2014/0088159 A1 | 3/2014 | Drummond et al. |
| 2014/0155439 A1 | 6/2014 | Donald et al. |
| 2014/0163042 A1 | 6/2014 | Davidson et al. |
| 2015/0126534 A1 | 5/2015 | Davidson et al. |

FOREIGN PATENT DOCUMENTS

| EA | 016312 B1 | 4/2012 |
| EP | 0505321 A2 | 9/1992 |
| WO | 2003/068746 A1 | 8/2003 |
| WO | 2003068747 A1 | 8/2003 |
| WO | 2003/076405 A1 | 9/2003 |
| WO | 2007/129040 A1 | 11/2007 |
| WO | 2009/060160 A1 | 5/2009 |
| WO | 2009106844 A1 | 9/2009 |
| WO | 2014/001802 A1 | 1/2014 |

(Continued)

OTHER PUBLICATIONS

Lasek. Cancer Immunology, Immunotherapy, 2014, 63, 419-433 (Year: 2014).*
Lu, Hailing; "TLR Agonists for Cancer Immunotherapy: Tipping the Balance Between the Immune Stimulatory and Inhibitory Effects"; Frontiers in Immunology, Mar. 3, 2014; vol. 5, Article 83.
Heckel, Mark C., et al.; "Human Breast Tumor Cells Express IL-10 and IL-12p40 Transcripts and Proteins, but do not produce IL-12p70"; Cellular Immunology 266 (2011) 143-153.
Song et al (2009) JCI 119, 1524-1536.
Song et al. (2012) Experimental and Therapeutic Medicine 3(2), 319-323.
Szaflarska et al(2009) Anticancer Research 29, 5005-5012.

(Continued)

*Primary Examiner* — Noble E Jarrell
(74) *Attorney, Agent, or Firm* — Norton Rose Fulbright US LLP

(57) ABSTRACT

The present invention relates to a compound and composition for use in the stimulation of IL-12 production and IFN-γ production, which compound is selected from: tert-butyl N-[2-{4-[6-amino-5-(2,4-difluorobenzoyl)-2-oxopyridin-1 (2H)-yl]-3,5-difluorophenyl}ethyl)-L-alaninate, or a pharmaceutically acceptable salt, hydrate or solvate thereof; and N-[2-{4-[6-amino-5-(2,4-difluorobenzoyl)-2-oxopyridin-1 (2H)-yl]-3,5-difluorophenyl}ethyl)-L-alanine.

24 Claims, No Drawings

(56) References Cited

FOREIGN PATENT DOCUMENTS

| WO | 2014/060742 A1 | 4/2014 |
|---|---|---|
| WO | 2014/170677 A1 | 10/2014 |

OTHER PUBLICATIONS

Tian et al. (2011) Int. J Gynecol. Cancer 21(9), 1672-1678.
Underwood et al, "SB 239063 a Potent p38 MAP Kinase Inhibitor, Reduces Inflammatory Cytokine Production, Airways Eosinophil Infiltration, and Persistence", J. Pharmacol. Exp. Ther., vol. 293, No. 1, 2000, pp. 281-288.
Van Herpen et al. (2004) Clinical Cancer Research 10 (8) 2626-2635.
Van Roon et al, "Selective Elimination of Synovial Inflammatory Macrophages in Rheumatoid Arthritis by an Fcy Receptor I-Directed Immunotoxin", Arthritis & Rheumatism, vol. 48, No. 5, 2003, pp. 1229-1238.
Vetter et al. (2009) J Neuropathol. Exp. Neurol. 68(5), 525-534.
Vuk-Pavlovic (2010) Prostate 70, 443-455.
Wadsworth et al, "RWJ 67657, a Potent, Orally Active Inhibitor of p38 Mitogen-Activated Protein Kinase", J. Pharmacol. Exp. Ther., vol. 291, No. 2, 1999, pp. 680-687.
Waetzig et al, "p38 Mitogen-Activated Protein Kinase Is Activated and Linked to TNF-a Signaling in Inflammatory Bowel Disease", J. Immunol., No. 168; 2002; pp. 5342-5351.
Wigginton et al. (1996) Journal of the National Cancer Institute 88(1), 38-43.
Yang et al, "Evidence of a central role for p38 map kinase induction of tumor necrosis factor ? in pancreatitis-associated pulmonary injury", Surgery, vol. 126, 1999, pp. 216-222.
Zaharoff et al. (2009) Cancer Res. 69(15), 6192-9.
Zhang et al (2000) The Journal of Immunology, 165, 1374-1380.
Ali et al (2012) Journal of Immunotoxicology 9, 168-172.
Baessler et al. (2009) Cancer Res. 69, 1037-1045.
Barone et al, "SB 239063, a Second-Generation p38 Mitogen-Activated Protein Kinase Inhibitor, Reduces Brain Injury and Neurological Deficits in Cerebral Focal Ischemia", J. Pharmacol. Exp. Ther., No. 296, 2001, pp. 312-321.
Behr et al, "Hypertensive End-Organ Damage and Premature Mortality Are P38 Mitogen-Activated Protein Kinase-Dependent in a Rat Model of Cardiac Hypertrophy and Dysfunction", Circulation, No. 104, 2001, pp. 1292-1298.
Bekaii-Saab et al. (2009) Mol. Chancer. Ther. 8(11), 2983-2991.
Bockholt et al. (2012) J. Urol. 187, 2228-2235.
Borsch et al, "The Cyanohydridoborate Anion as a Selective Reducing Agent", J. Am. Chem. Soc., No. 93(23), 1971, pp. 2897-2904.
Caminschi et al. (1998) Am. J. Respir. Cell Mol Biol. 1998, 19(5), 738-746.
Colombo et al: "Interleukin-12 in anti-tumor immunity and immunotherapy", Cytokine and Growth Factor Reviews, vol. 13, No. 2, Apr. 1, 2002 (Apr. 1, 2002), pp. 155-168.
Cuenda et al, "SB203580 is a specific inhibitor of a MAP kinase homologue which is stimulated by cellular stresses and interleukin-1", FEBS Lett., No. 364, 1995, pp. 229-233.
Cui et al (2007) Cancer Immunol. Immunother. 56(12), 1993-2001.
Denham et al, "Inhibition of p38 mitogen activate kinase attenuates the severity of pancreatitis-induced adult respiratory distress syndrome", Crit. Care Med., vol. 28, No. 7, 2000, pp. 2567-2572.
Dodeller et al (2005) Eur. J. Immunol. 35(12), 3631-3642.
Dubey et al. (2007) Endocrinology 148(9), 4125-4127.
Engel et al, "Leptomycin B-sensitive nuclear export of MAPKAP kinase 2 is regulated by phosphorylation", EMBO J., No. 17, No. 12, 1998, pp. 3363-3371.
Ferretti et al. (2010) Immunol. Lett. 133(2), 99-105.
Foster et al, "Potential of p38 Inhibitors in the Treatment of Rheumatoid Arthritis", Drug News Perspect, No. 13(8), 2000, pp. 488-497.
Gabrusiewicz et al (2011) PLoS ONE 6(8), e23902.
Gillies et al. (1998) J Immunol. 160(12), 6195-6203.
Haku et al. (1997) Cytokine 9(11), 846-852.
Han et al, "A MAP Kinase Targeted By Endotoxin and Hyperosmolarity in Mammalian Cells", Science, vol. 265, 1994, p. 808.
Harada et al. (2004) J. Immunol. 2004,173, 6635-6644.
Jahn et al. (2012) PLoS ONE 7(9), e44482.
Jiang et al, Characterization of the structure and function of a New Mitogen-activated Protein Kinase (p38β), J. Biol. Chem., vol. 271, No. 30, 1996, pp. 17920-17926.
Jiang et al, Characterization of the structure and Function of the Fourth Member of p38 Group Mitogen-activated Protein Kinases, p38?, J. Biol. Chem., vol. 272, No. 48, 1997, pp. 30122-30128.
Kotlyarov et al, "MAPKAP kinase 2 is essential for LPS-induced TNF—a biosynthesis", Nat. Cell Biol., vol. 1, 1999, pp. 94-97.
Kumar et al, "P38 Map Kinases: Key Signalling Molecules As Therapeutic Targets For Inflammatory Diseases", Nature Reviews Drug Discovery, vol. 2, 2003, pp. 717-726.
Kundu et al (2017) PNAS 114, 11482-11487.
Lebel, "The Addition of Nitrones to Olefins. Fused Bicyclic Isoxazolidines", J. Am. Chem. Soc., vol. 86, 1964, pp. 3759-3767.
Li et al, "The Primary Structure of p38g: A New Member of p38 Group of MAP Kinases", Biochem. Biophys. Res. Commun., No. 228, 1996, pp. 334-340.
Lisiero et al. (2011) J. Immunol. 186(9), 5068-5077.
Ma et al. (2001) J Biol Chem 276, 13664-13674.
Mantovani (2010) Eur J Immunol 40, 3317-3320.
Marriot et al. (2001) Clin. Exp. Immunol. 125, 64-70.
Mazzolini et al. (1999) Cancer Gene Therapy 6(6), 514-522.
Meng et al, "Structure of Mitogen-activated Protein Kinase-activated Protein (MAPKAP) Kinase 2 Suggests a Bifunctional Switch That Couples Kinase Activiation with Nuclear Export", J. Biol. Chem., vol. 277, No. 40, 2002, pp. 37401-37405.
Mitsunobu et al, "Preparation of Esters of Carboxylic and Phosphoric Acid via Quaternary Phosphonium Salts", Bull. Chem. Soc. Jpn., vol. 40, No. 10; 1967; pp. 2380-2382.
Mori et al. (2011) Cancers 3, 3726-3739.
Naldini et al, "Role of Inflammatory Mediators in Angiogenesis", Current Drug Targets, Inflammation & Allergy, No. 4, 2005, pp. 3-8.
Needham et al: "Drug targeting to monocytes and macrophages using esterase-sensitive chemical motifs", Journal of Pharmacology and Experimental Therapeutics, vol. 339, No. 1, Oct. 1, 2011 (Oct. 1, 2011), pp. 132-142.
Porter et al. (2007) Nature Reviews Drug Discovery, 6, 231-248.
Pützer et al. (2002) Mol. Ther. 5(4), 405-412.
Rakhmilevich et al. (2000) Cancer Gene Ther. 7(6) 826-838.
Revesz et al, "SAR of 4-Hydroxypiperidine and Hydroxyalkyl Substituted Heterocycles as Novel p38 Map Kinase Inhibitors", Biorg. Med. Chem. Lett., No. 10, 2000, pp. 1261-1264.
Ruffell et al. (2014) Cancer Cell 26, 1-15.
Salituro et al, "Inhibitors of p38 MAP Kinase: Therapeutic Intervention in Cytokine-Mediated Diseases", Current Medicinal Chemistry, No. 6, 1999, pp. 807-823.
Schirok et al, "Efficient Regioselective Synthesis of 6-Amino-5-benzoyl-1-Substituted 2(1H)-Pyridinones", J. Org. Chem., No. 70, 2005, pp. 9463-9469.
Shi et al. (2005) Tumori 91(6), 531-538.
Sica et al. (2000) J Immunol, 164, 762-767.
Silver et al. (1999) Gynecologic Oncology 72(2), 154-160.
Gura T., Systems for identifying new drugs are often faulty, Science, 1997, v.278, n.5340, p. 1041-1042.
Jain R.K., Barriers to drug delivery in solid tumors, Sci. Am., 1994, v.271, n.1, p. 58-65.

* cited by examiner

TREATMENT OF CANCER BY STIMULATION OF IL-12 PRODUCTION

CROSS-REFERENCE TO RELATED APPLICATIONS

This application is a national phase application under 35 U.S.C. § 371 that claims priority to International Application No. PCT/GB2018/052448 filed Aug. 30, 2018, which claims priority to United Kingdom Patent Application No. 1713975.9, filed Aug. 31, 2017, both of which are incorporated herein by reference in their entirety.

FIELD OF THE INVENTION

The invention relates to compounds for use in the stimulation of IL-12 production and IFN-γ production.

BACKGROUND OF THE INVENTION

Interleukin 12 (IL-12) is a pleiotropic cytokine, the actions of which create an interconnection between the innate and adaptive immunity. Due to bridging the innate and adaptive immunity and potently stimulating the production of IFN-γ—a cytokine coordinating natural mechanisms of anticancer defense, IL-12 is an important cytokine in the tumour microenvironment. The main source of IL-12 in humans are activated antigen-presenting cells, such as dendritic cells and hematopoietic phagocytes (monocytes, macrophages, and also neutrophils). The bioactive heterodimer IL-12 p70 acts on NK and T cells to increase production of IFN-γ, which is the most potent mediator of IL-12 actions. Other important elements of IL-12 actions are as follows: stimulation of growth and cytotoxicity of activated NK cells, CD8+ and CD4+ T cells, shifting differentiation of CD4+ Th0 cells toward the Th1 phenotype; enhancement of antibody-dependent cellular cytotoxicity (ADCC) against tumor cells; and the induction of IgG and suppression of IgE production from B cells. Several other mechanisms, however, also strongly contribute to antitumor activities of IL-12. These are potent antiangiogenic effects via induction of antiangiogenic cytokine and chemokine production, remodeling of the peritumoral extracellular matrix and tumor stroma, reprogramming of myeloid-derived suppressor cells, and changes in processing and increasing expression of MHC class I molecules. All the above mechanisms converge during response against tumors and are postulated to be responsible for the high potency of antitumor effects of IL-12.

IL-12 is known to be beneficial in the treatment of several cancers as set out below.

Head and neck cancers: In a study of 30 patients with previously untreated HNSCC, injection of recombinant IL-12 into the primary tumor was shown to increase the number of natural killer cells and alter the distribution of B cells in the lymph nodes of the 10 treated patients. These effects included redistribution of lymphocytes from the peripheral blood to the lymph nodes in the neck; a significant increase in natural killer cells and a lower percentage of cells in the lymph nodes and the primary tumor; and a 128-fold increase in IFNγ-mRNA in the lymph nodes. Finally, the Th2 profile in the lymph nodes of IL-12-treated patients switched to a Th1 profile. (C. M. Van Herpen, M. Looman, M. Zonneveld et al., "Intratumoral administration of recombinant human interleukin 12 in head and neck squamous cell carcinoma patients elicits a T-Helper 1 profile in the locoregional lymph nodes," Clinical Cancer Research, 10 (8) 2626-2635, 2004.)

Melanoma: IL-12-primed effector T cells dramatically reduced the growth in mice of well-established s.c. B16-F10 melanoma tumors and significantly increased survival to highly immune resistant, established intracranial tumors. Control of tumor growth by CD8+ T cells was dependent on IL-12-mediated upregulation of the high-affinity IL-2R (CD25) and a subsequent increase in the sensitivity to IL-2 stimulation. Finally, IL-12-primed human PBMCs generated tumor specific T cells both phenotypically and functionally similar to IL-12-primed mouse tumor-specific T cells. (D. N. Lisiero, H. Soto, L. M. Liau and R. M. Prins Enhanced "Sensitivity to IL-2 Signaling Regulates the Clinical Responsiveness of IL-12-Primed CD8+ T Cells in a Melanoma Model" J Immunol 2011, 186 (9) 5068-5077.)

Renal: IL-12 administered in combination with pulse IL-2 induced rapid and complete regression of primary and metastatic Renca tumors (J. M. Wigginton, K. L., Komschlies, T. C. Back, J. L. Franco, M. J., Brunda, R. H. Wiltrout "Administration of Interleukin, 12 With Pulse Interleukin 2, and the Rapid and Complete, Eradication of Murine, Renal Carcinoma" Journal of the National Cancer Institute, 1996, 88(1), 38-43.)

Prostate: Specific targeting of a human IL-12 fusion protein to metastatic prostate carcinoma xenografts was also shown to be effective in SCID mice transplanted with human lymphocyte-activated killer cells. (S. D. Gillies, Y. Lan, J. S. Wesolowski, X. Qian, R. A. Reisfeld, S. Holden, M. Super and K-M. Lo "Antibody-IL-12 Fusion Proteins Are Effective in SCID Mouse Models of Prostate and Colon Carcinoma Metastases" J Immunol. 1998, 160(12), 6195-6203.)

Breast: Interleukin-12 (IL-12) gene therapy induced strong antitumor effects in several syngeneic murine tumor models including 4T1 mammary adenocarcinoma. (Rakhmilevich A L, Janssen K, Hao Z, Sondel P M, Yang N-S. "Interleukin 12 gene therapy of a weakly immunogenic mouse mammary carcinoma results in reduction of spontaneous lung metastases via a T cell independent mechanism" Cancer Gene Ther 2000, 7(6), 826-38.)

Bladder: In anti-tumor studies, 88% to 100% of mice bearing orthotopic bladder tumors were cured after four intravesical treatments with chitosan/IL-12. 38% to 60% of mice treated with IL-12 alone. (D. A. Zaharoff, B. S. Hoffman, H. B. Hooper, C. J. Benjamin Jr., K. K. Khurana, K. W. Hance, C. J. Rogers, P. A. Pinto, J. Schlom and J. W. Greiner "Intravesical Immunotherapy of Superficial Bladder Cancer with Chitosan/Interleukin-12" Cancer Res 2009, 69(15), 6192-9.)

Ovarian: Murine IL-12 treatment resulted in significant tumor growth delay and tumor regression in SCID mice engrafted with human ovarian cancer. (D. F. Silver, R. E. Hempling, M. S. Piver, E. A. Repasky "Effects of IL-12 on Human Ovarian Tumors Engrafted into SCID Mice" Gynecologic Oncology, 1999, 72(2), 154-160.)

Pancreatic: Single intratumoral injection of AdIL-12/B7.1 led to a prolonged immune response and mediated complete regression in 80% of treated animals in a model of murine model of ductal pancreatic cancer. (Pitzer B. M., Rödicker F., Hitt M. M., Stiewe T., Esche H. Improved treatment of pancreatic cancer by IL-12 and B7.1 costimulation: antitumor efficacy and immunoregulation in a nonimmunogenic tumor model. Mol. Ther. 2002, 5(4), 405-12.)

Acute Myeloid Leukaemia: In vivo experiments were performed using SCID-NOD mice injected intraperitoneally (i.p.) with the human U937 AML cell line and subsequently treated with human recombinant IL-12 or PBS i.p. Histological, immunohistochemical and flow cytometric analyses on explanted tumors revealed that IL-12 reduced new vessel formation, induced apoptosis and inhibited tumor cell proliferation. (Ferretti E, Di Carlo E, Cocco C, Ribatti D, Sorrentino C, Ognio E, Montagna D, Pistoia V, Airoldi I. "Direct inhibition of human acute myeloid leukemia cell growth by IL-12" Immunol Lett. 2010, 133(2), 99-105.)

Cervical: IL-21 and IL-12 significantly elevated PBMC cytotoxicity against cervical carcinoma SiHa cells. Moreover, IL-21 plus IL-12 significantly elevated PBMC cytotoxicity in comparison to IL-21 alone and IL-12 alone. We also found that IL-21 plus IL-12 significantly decreased Treg and TH17 cell proportion in comparison to controls. Notably, IL-21 plus IL-12 significantly decreased TH17 cell proportion in comparison to IL-21 alone. (Tian Y, Yuan C, Ma D, Zhang Y, Liu Y, Zhang W, Hou F, Cui B "IL-21 and IL-12 inhibit differentiation of Treg and TH17 cells and enhance cytotoxicity of peripheral blood mononuclear cells in patients with cervical cancer" Int J Gynecol Cancer 2011 21(9), 1672-8.)

Glioma: Glioma rejection was significantly enhanced in mice expressing IL-12 in the CNS and was predominantly dependent on the presence of CD8+ T cells as measured by rejection of GL261 cells in a syngenic mouse glioma model. (Vetter M, Hofer M J, Roth E, Pircher H P, Pagenstecher A "Intracerebral interleukin 12 induces glioma rejection in the brain predominantly by CD8+ T cells and independently of interferon-gamma" J Neuropathol Exp Neurol. 2009 May; 68(5):525-34.)

Lung: Peripheral blood mononuclear cells from lung cancer patients exhibited cell killing activity after in vitro incubation with IL-12 for 4 days. Effective killer induction by IL-12 was observed even in mononuclear cells from advanced lung cancer patients and patients with small cell lung cancer. IL-12 and a suboptimal dose of IL-2 had additive effects in inducing killer activity in mononuclear cells from both lung cancer patients and control subjects. Addition of IL-12 alone or in combination with IL-2 resulted in interferon (IFN)-gamma production by MNC from lung cancer patients as well as control subjects. These observations suggest that IL-12 could be useful for immunotherapy of lung cancer in humans. (Haku T, Yanagawa H, Nabioullin R, Takeuchi E, Sone S. "Interleukin-12-mediated killer activity in lung cancer patients" Haku T., Yanagawa H., Nabioullin R., Takeuchi E., Sone S. Cytokine 1997, 9(11), 846-52.)

Gastric: A DC vaccine transfected with gastric cancer cell total ribonucleic acid (RNA) carrying the 4-1 BBL gene has a strong ability to kill gastric cancer cells through promoting T cell proliferation and enhancing the ability of cytotoxic T lymphocytes (CTLs) to kill gastric carcinoma cells and to secrete IL-12 and IFN-γ. (Z. Song, C. Guo, Y. Li, B. Tan, L. Fan and J. Xiao, "Enhanced antitumor effects of a dendritic cell vaccine transfected with gastric cancer cell total RNA carrying the 4-1BBL gene in vitro" Experimental and Therapeutic Medicine 2012, 3, 319-323.)

Hepatocellular carcinoma: In mice inoculated with MH134 cells, intratumoral gene transfer of mIL-12 elevated intratumoral mIL-12, IFN-γ, and IFN-γ-inducible protein-10, significantly reduced the number of microvessels and inhibited the growth of HCC. (N. Harada, M Shimada, S Okano, T Suehiro, Y Soejima, Y Tomita and Yoshihiko Maehara "IL-12 Gene Therapy Is an Effective Therapeutic Strategy for Hepatocellular Carcinoma in Immunosuppressed Mice" J Immunol 2004, 173, 6635-6644.)

Colon: In vivo gene therapy of colon cancer nodules by intratumoral injection of AdCMVIL-12 to mice inoculated with colon cancer CT26 cells induced a local increase in IL-12 and interferon-gamma levels and a complete regression of the tumor in 26 of 34 (76%) mice. Tumor disappeared between days 7 and 10 after vector administration. The antitumoral effect was mediated by CD8+ T cells and was associated with the generation of cytotoxic T lymphocytes against colon cancer cells. (G. Mazzolini, C. Qian, X. Xie, Y. Sun, J. Lasarte, M. Drozdzik and J. Prieto "Regression of colon cancer and induction of antitumor immunity by intratumoral injection of adenovirus expressing interleukin-12" Cancer Gene Therapy, 1999, 6(6), 514-522.)

Mesothelioma: The effects of rIL-12 on murine antitumor immune responses, using a nonimmunogenic murine MM tumor cell line (AB1) in vivo were studied. Systemic administration of rIL-12 at the time of tumor inoculation prevented AB1 tumor growth in up to 70% of treated mice, 50% of which were still resistant to AB1 upon rechallenge, indicating that long-term immunologic antitumor effects had been established. This rIL-12-induced effect was dependent on the involvement of both CD4(+) and CD8(+) but not natural killer (NK) cells. (Caminschi I, Venetsanakos E, Leong C C, Garlepp M J, Scott B, Robinson B W "Interleukin-12 induces an effective antitumor response in malignant mesothelioma" Am. J. Respir. Cell Mol Biol. 1998, 19(5):738-46.)

Multiple Myeloma: The expression vector pcDNA-IL-12 was generated and transfected into J558 myeloma cells and then bone marrow-derived DCs were fused with engineered J558/IL-12 cells. The antitumor immunity derived from vaccination of the fusion hybrid DC/J558/IL-12 was evaluated in vitro and in vivo. DC/J558/IL-12 cells secreted recombinant IL-12 (1.6 ng/mL), and inoculation of BALB/c mice with DC/J558/IL-12 hybrid induced a Th1 dominant immune response and resulted in tumor regression. Immunization of mice with engineered DC/J558/IL-12 hybrid elicited stronger J558 tumor-specific cytotoxic T lymphocyte (CTL) responses in vitro as well as more potent protective immunity against J558 tumor challenge in vivo than immunization with the mixture of DCs and J558/IL-12, J558/IL-12 and J558, respectively. Furthermore, the antitumor immunity mediated by DC/J558/IL-12 tumor cell vaccination in vivo appeared to be dependent on CD8+ CTL. (Shi M, Su L, Hao S, Guo X, Xiang J "Fusion hybrid of dendritic cells and engineered tumor cells expressing interleukin-12 induces type 1 immune responses against tumor" Tumori 2005, 91(6), 531-8.)

Lymphoma: A tumor-targeted IL12-IL2 fusion protein was superior in activating resting T cells to amplify and secrete pro-inflammatory cytokines compared to targeted IL2 or IL12 alone. NK cells were also activated by the dual cytokine protein to secrete IFN-γ and to lyse target cells. The tumor-targeted IL12-IL2, when applied by i.v. injection to immune-competent mice with established antigen-positive lymphoma tumors, accumulated at the tumor site and induced tumor regression. (T. Jahn, M. Zuther, B. Friedrichs, C. Heuser, S. Guhlke, H. Abken, A. Hombach An IL12-IL2-Antibody Fusion Protein Targeting Hodgkin's Lymphoma Cells Potentiates Activation of NK and T cells for an Anti-Tumor Attack PLoS ONE 7(9): e44482.)

Esophageal cancer: IL-12 in combination with trastuzumab and paclitaxel exhibits an acceptable toxicity profile and has activity in patients with HER2-overexpressing cancers including esophageal cancer. (Bekaii-Saab T S, Roda J M, Guenterberg K D, Ramaswamy B, Young D C, Ferketich A K, Lamb T A, Grever M R, Shapiro C L, Carson W E 3rd. "A phase I trial of paclitaxel and trastuzumab in combination with interleukin-12 in patients with HER2/neu-expressing malignancies" Mol Cancer Ther. 2009, 8(11), 2983-91.)

Thyroid cancer: IL-12 in combination with trastuzumab and paclitaxel exhibits an acceptable toxicity profile and has activity in patients with HER2-overexpressing cancers including thyroid cancer. (Bekaii-Saab T S, Roda J M, Guenterberg K D, Ramaswamy B, Young D C, Ferketich A K, Lamb T A, Grever M R, Shapiro C L, Carson W E 3rd. "A phase I trial of paclitaxel and trastuzumab in combination with interleukin-12 in patients with HER2/neu-expressing malignancies" Mol Cancer Ther. 2009, 8(11), 2983-91.)

WO 2007/129040, WO 2009/060160 and WO 2014/060742 disclose alpha amino acid esters that are inhibitors of p38 MAP kinase. The compounds disclosed are stated to be potent and selective inhibitors of p38 MAPK (p38α, β, γ, and δ) and the isoforms and splice variants thereof especially p38α, p38β and p38β2.

WO 2007/129040 also disclosed that the compounds with which it is concerned include those which selectively accumulate in macrophages. WO 2009/060160 discloses a group of specific compounds falling within the general disclosures of WO 2007/129040, but not specifically identified or exemplified therein. The compounds display the macrophage selectivity property discussed above.

WO 2014/060742 discloses the compound tert-butyl N-[2-{4-[6-amino-5-(2,4-difluorobenzoyl)-2-oxopyridin-1(2H)-yl]-3,5-difluorophenyl}ethyl)-L-alaninate and the corresponding acid compound N-[2-{4-[6-amino-5-(2,4-difluorobenzoyl)-2-oxopyridin-1(2H)-yl]-3,5-difluorophenyl}ethyl)-L-alanine. These compounds were found to be particularly good at inhibiting p38 MAP kinase activity.

SUMMARY OF THE INVENTION

IL-12 is known to be beneficial in the treatment of several cancers and the stimulation of IL-12 production is a promising development in the treatment of cancer. It is known that inhibition of p38 leads to inhibitory effects on TNF-α, IFN-γ and IL-10, although the immunomodulation of p38 MAPK inhibitors is still poorly understood. The role of p38 inhibitors in IL-12 production is an area of ongoing research.

The effect of p38 MAPK inhibitors on IL-12 production by monocytes, macrophages and dendritic cells is thought to be dependent on the presence of IFN-γ. Studies into the role of p38 in T-cell function have been carried out using the known p38 inhibitor SB203580 (S Zhang et al., The Journal of Immunology, 2000, 165, 1374-1380). These studies have shown that IL-12 activates p38 MAPK and suggests that IL-12-activated p38 MAPK is required for IL-12-induced IFN-γ expression.

A report by Marriott et al (Marriot et al, Clin Exp Immunol 2001; 125:64-70) found that a p38 MAPK inhibitor, selective for inhibition of p38 MAPK, up-regulated IL-12 production. However, IFN-γ priming was essential and no increase in IL-12 was seen in the absence of exogenous IFN-γ in isolated macrophages and monocytes. In whole blood and PBMC assays sufficient IFN-γ priming was provided by the lymphocyte population but while IL-12 production was enhanced the production of IFN-γ was inhibited.

One of the main anti-tumour actions of IL-12 is increasing production of IFN-γ by T-cells. There is little benefit in elevating IL-12 if it does not translate to elevated levels of IFN-γ and the immune consequences that flow from that increase. The art clearly teaches that p38 inhibition suppresses IL-12 induced IFN-γ expression. p38 MAPK inhibitors would not, therefore be expected to provide beneficial anti-tumour immune effects since the decreased IFN-γ production would be detrimental in this regard. As such p38 MAPK inhibitors would not be identified as suitable candidates for further investigation in the treatment of cancers by immunomodulation, in particular in cancers affected by IL-12 production.

The compound used in the invention, a p38 inhibitor, has, however, been found to provide the combined advantages of both increased IL-12 production and increased IFN-γ production and is therefore expected to be pharmacologically effective in the treatment of cancers where increased IL-12 production is beneficial. Given the known use of the compound as a p38 inhibitor this finding is entirely unexpected. Moreover, the magnitude of IL-12 production has been found to be significantly higher than that observed for conventional p38 inhibitors. Notably, the compound increases production of IL-12p70, the bioactive heterodimer which is the most beneficial in achieving immune response: many earlier reports for conventional compounds show effects only in IL-12p40. The finding provides a previously unrecognized use of the compound, in the treatment of cancers where elevated levels of IL-12 is key, opening up new treatment pathways and new clinical situations in which the compound may find therapeutic application.

Specifically, the present inventors have found that tert-butyl N-[2-{4-[6-amino-5-(2,4-difluorobenzoyl)-2-oxopyridin-1(2H)-yl]-3,5-difluorophenyl}ethyl)-L-alaninate, a known p38 MAPK inhibitor, leads to the stimulation of IL-12 production (e.g. IL-12p70 production), in particular the compound provides unexpectedly high levels of IL-12 in cell. Preferably, the compound provides unexpectedly high levels of IL-12p70 in cell.

This is understood to be achieved via IL-12 driven INF-γ production. Elevated levels of IL-12 and INF-γ provide significant benefits in the treatment of cancer, in particular cancers in which the tumour associated cells are IL-12 low phenotype cells.

This compound had been identified previously as useful in the treatment of cell proliferative diseases such as cancer where control of the cytokine IL10 is key. That the same compound controls the production of cytokine IL10 and enables an increase in IL-12 via an entirely separate process by which IL-12 induced IFN-γ expression occurs could not have been foreseen.

The fact that the compound provides an additional, unexpected, immune effect means that it could be used to provide a more effective treatment for existing patients and/or treat new patient groups. The compound could, for example, be used in the treatment of patients where controlling the production of cytokine IL10 alone would have been considered ineffective or in some way insufficient. Examples include the use of the compound in the treatment of particularly aggressive cancers or in the treatment of patients where alternative drugs have failed, e.g., because of the need to both control the production of cytokine IL10 and increase IL-12 production in order to provide an effective treatment.

Accordingly, the present invention provides a compound for use in the stimulation of IL-12 production and IFN-γ production, which compound is selected from: tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof; and N-[2-{4-[6-amino-5-(2,4-difluorobenzoyl)-2-oxopyridin-1(2H)-yl]-3,5-difluorophenyl}ethyl)-L-alanine.

Also provided by the invention is a composition for use in the stimulation of IL-12 production and IFN-γ production, wherein the composition comprises a compound as defined herein together with one or more pharmaceutically acceptable carriers and/or excipients.

The invention also provides a compound for use in the prevention or treatment of a cell proliferative disease by stimulation of IL-12 production, which compound is selected from: tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof; and N-[2-{4-[6-amino-5-(2,4-difluorobenzoyl)-2-oxopyridin-1(2H)-yl]-3,5-difluorophenyl}ethyl)-L-alanine. Preferably the compound is for use in the stimulation of IL-12 production and IFN-γ production.

Also provided by the invention is a method of stimulating IL-12 production and IFN-γ production in a subject, which method comprises administering to said subject an effective amount of a compound as defined herein or a composition as defined herein. Also provided is a method for the prevention or treatment of a cell proliferative disease by stimulation of IL-12 production, which method comprises administering to said subject an effective amount of a compound as defined herein or a composition as defined herein.

Further provided by the invention is the use of a compound as defined herein or a composition as defined herein in the manufacture of a medicament for stimulation of IL-12 production and IFN-γ production. Also provided is the use of a compound as defined herein or a composition as defined herein in the manufacture of a medicament for the prevention or treatment of a cell proliferative disease by stimulation of IL-12 production.

As it was previously known that the compound could be used in the treatment of cancers in which the control of IL-10 levels is key, the present invention not only provides a new use for the compound but also provides a compound that has the potential to treat a new spectrum of cancers via the ability to advantageously control the level of both IL-10 and IL-12 with a single active agent.

DETAILED DESCRIPTION OF THE INVENTION

The invention relates to the use of a compound, which compound is (i) tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof (referred to herein as the ester compound); or (ii) N-[2-{4-[6-amino-5-(2,4-difluorobenzoyl)-2-oxopyridin-1(2H)-yl]-3,5-difluorophenyl}ethyl)-L-alanine (referred to herein as the acid compound).

Preferably, the compound is the ester compound, i.e. tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

The ester compound may be prepared in the form of a salt, hydrate or solvate. Typically, the salt is a pharmaceutically acceptable salt.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, salicylic, glutamic, lactic, fumaric, maleic, malic, ascorbic, succinic, tartaric, benzoic, acetic, methanesulphonic, ethanesulphonic, benzenesulphonic or p-toluenesulphonic acid. The pharmaceutically acceptable acid may in particular be a dicarboxylic acid, e.g. tartaric, citric, glutamic, maleic, malic, succinic, fumaric, oxalic or adipic acid. Pharmaceutically acceptable bases include alkali metal (e.g. sodium or potassium) and alkali earth metal (e.g. calcium, barium or magnesium) hydroxides and organic bases such as alkyl amines, aralkyl amines and heterocyclic amines. Examples of suitable organic bases include, but are not limited to, N-methyl-D-glucamine, choline tris(hydroxymethyl)aminomethane, L-arginine, L-lysine, N-ethyl piperidine, dibenzylamine. For a review on suitable salts, see Handbook of Pharmaceutical Salts: Properties, Selection, and Use by Stahl and Wermuth (Wiley-VCH, Weinheim, Germany, 2002).

Preferably, the pharmaceutically acceptable salt is the methanesulfonate or ethanesulphonate salt. More preferably, the pharmaceutically acceptable salt is the ethanesulphonate salt.

The term 'solvate' is used herein to describe a molecular complex comprising the compound and a stoichiometric amount of one or more pharmaceutically acceptable solvent molecules, for example, ethanol. The term 'hydrate' is employed when said solvent is water.

For the avoidance of doubt, the compound may be used in any tautomeric form.

The acid compound is the metabolite of the ester. Thus, on administration of an ester to a subject, the ester is hydrolysed to provide the acid within the cell.

The compound includes a chiral centre. The compound is typically in the form of the L-alanine or L-alaninate derivative (i.e. as depicted in Example 1). However, the compound may exist as the D-alanine or D-alaninate derivative or as a mixture of the D- and L-forms. Where a mixture is present, preferably at least 90%, 95% or 99% is present as the L-form.

A suitable scheme and process for the production of the compound, with reference to the examples section which follows, is discussed below.

The starting materials are typically 4-Chlorophenyl 3-(2,4-difluorophenyl)-3-oxopropanimidothioate hydro-chloride and 2-(4-Amino-3,5-difluorophenyl)ethanol. 2-(4-Amino-3,5-difluorophenyl)ethanol may be prepared using the following scheme, which is analogous to scheme 1 of the examples section:

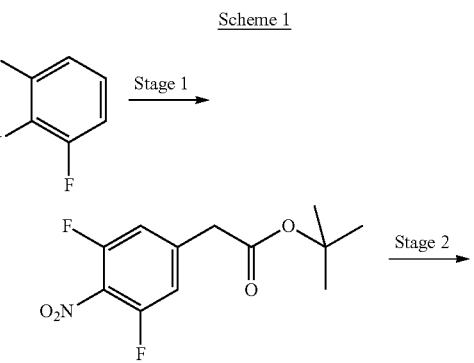

Scheme 1

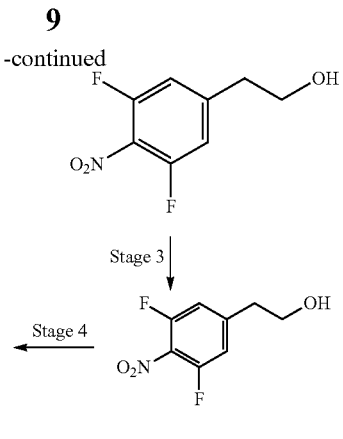

Intermediate 2

Difluoronitrobenzene is commercially available. Stage 1 requires the addition of a tert-butyl acetate group to the phenyl ring, para to the nitro group. Stage 2 requires the hydrolysis of the ester group to form the corresponding acid. The acid is reduced to a primary alcohol in stage 3. In stage 4 the nitro group is reduced to an amine.

4-Chlorophenyl 3-(2,4-difluorophenyl)-3-oxopropanimidothioate hydro-chloride may be prepared using experimental procedures described in WO 2003076405.

The ester compound may then be synthesised using the following scheme, which is analogous to scheme 2 of the examples section.

piolic acid is added to form 2-{4-[6-Amino-5-(2,4-difluorobenzoyl)-2-oxopyridin-1(2H)-yl]-3,5-difluorophenyl}ethyl acetate. In stage 3, the acetate group is hydrolysed to leave an alcohol and in stage 4 the resulting alcohol group is oxidised to an aldehyde. The compound of the invention is then formed in stage 5, by the addition of tert-butyl L-alaninate hydrochloride. Tert-butyl L-alaninate hydrochloride is commercially available.

The acid compound may be prepared by hydrolysis of the ester compound.

The invention also provides a pharmaceutical composition comprising the compound, typically the ester compound, together with one or more pharmaceutically acceptable carriers and/or excipients. Said pharmaceutical composition typically contains up to 85 wt % of a compound of the invention. More typically, it contains up to 50 wt % of a compound of the invention. Preferred pharmaceutical compositions are sterile and pyrogen free.

The compounds may be administered in a variety of dosage forms. Thus, they can be administered orally, for example as tablets, troches, capsules, lozenges, aqueous or oily suspensions, dispersible powders or granules. The compounds may also be administered parenterally, either subcutaneously, intravenously, intramuscularly, intrasternally, transdermally or by infusion techniques. Administration may alternatively be intraperitoneal or buccal. Depending on the vehicle and concentration used, the drug can either be suspended or dissolved in the vehicle. Advantageously,

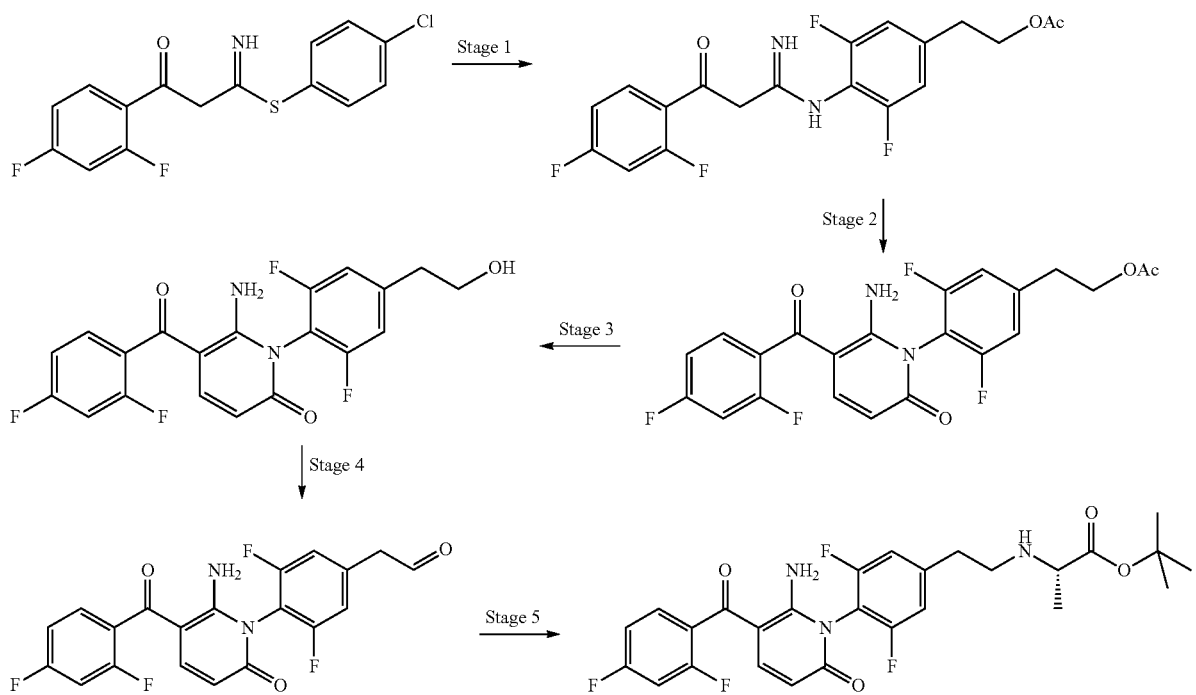

Example 1

In stage 1, the 2-(4-Amino-3,5-difluorophenyl)ethanol and 4-Chlorophenyl 3-(2,4-difluorophenyl)-3-oxopropanimidothioate hydro-chloride are reacted together to form 2-(4-{[3-(2,4-Difluorophenyl)-3-oxopropanimidoyl]amino}-3,5-difluorophenyl)ethyl acetate. In stage 2, proadjuvants such as a local anaesthetic, preservative and buffering agent can be dissolved in the vehicle. The compounds may also be administered as suppositories. The compounds may be administered by inhalation in the form of an aerosol via an inhaler or nebuliser.

The compound is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, tragacanth gums, gelatin, syrup, acacia, sorbitol, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in a known manner, for example, by means of mixing, granulating, tabletting, sugar-coating, or film coating processes.

Liquid dispersions for oral administration may be solutions, syrups, emulsions and suspensions. Liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water, alcohols and solubilising agents, e.g. cyclodextrins or modified cyclodextrins or preferably they may be in the form of sterile, aqueous, isotonic saline solutions. For example, solutions may contain as carrier sterile water and solubilising agents, e.g. cyclodextrins or modified cyclodextrins.

Preferred solvents for IV administration are ethanol, propylene glycol and cyclodextrins. The formulation, including one or more of said solvents, may be mixed with saline or aqueous dextrose solution (e.g. 5% dextrose solution) prior to administration. Alternatively it may be administered without further dilution.

Solubility in aqueous solutions may be increased by adding agents that alter the pH. In particular basic compounds may be converted to a salt by adding an organic or inorganic acid. This would increase solubility in aqueous solutions and reduce the pH. Suitable salts are those mentioned herein, in particular hydrochloride salts, sulphate salts and dicarboxylic acid salts (e.g. tartrate, citrate, glutamate, maleate, malate, succinate, fumarate, oxalate or adipate). These salts may be formed by addition of the corresponding acid, namely hydrochloric acid, sulphuric acid or a dicarboxylic acid, e.g. tartaric, citric, glutamic, maleic, malic, succinic, fumaric, oxalic or adipic acid.

The compound may be provided in a controlled release or slow release formulation. For instance, polymers such as glycolide, lactide (DL-lactide), caprolactone, and polyethylene glycol, and copolymers of any of these, may be used in such a formulation. Examples include poly DL-lactide, poly DL-lactide-co-glycolide, polycaprolactone and block copolymers or blends of polycaprolactone and polyethylene glycol.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

A therapeutically effective amount of the compound is administered to a subject. It will be understood that the specific dose level for any particular subject will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will usually be determined by clinical trial.

A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg. The compound is typically administered to the patient in a non-toxic amount.

The compound may be provided as a lipid-based formulation. As the skilled person will appreciate, the lipid-based formulation may vary depending on, for example, the route of administration and drug toxicity. Preferably, the lipid-based formulation will be for oral administration. The advantages of formulating the compound as a lipid-based drug include the potential to enhance bioavailability of the compound and/or increase the solubility of the compound (see, for example, Drug Discovery, 2007, 6:231-248).

The lipid-based formulation may, for example, comprise the compound and a lipophilic phase, optionally with at least one pharmaceutically acceptable surfactant and/or a pharmaceutically acceptable water miscible solvent. Preferably, the lipid-based formulation comprises a therapeutically effective amount of the compound.

In some embodiments, the compound may be provided in a soft gelatine capsule, or softgel, for oral administration. Examples of softgel technology include OptiGel™ and OptiShell™. Typically, the soft gelatine capsule will contain a liquid formulation comprising the compound. The liquid formulation may, for example, comprise the compound as a lipid-based drug. The soft gelatine capsule may, for example, comprise gelatine, water, an opacifier and a plasticiser (e.g. glycerine or sorbitol). The gelatine capsule may optionally be coated, for example, to assist with targeted delivery, to provide a modified release profile, to improve stability of the compound and/or to reduced side effects.

As mentioned above, the compound provides unexpectedly high levels of IL-12 in cell, i.e., the compound increases the level of IL-12 in cell. Preferably, the compound provides unexpectedly high levels of IL-12p70. It is the up-regulation of IL-12, and in particular IL-12p70, that provides particularly beneficial effects for the treatment of cell proliferative diseases.

In particular, stimulation of IL-12 production and IFN-γ production from human monocytes in peripheral blood mononuclear cell (human PBMC) samples, is observed. The present compounds are therefore able to increase production of both IL-12 (IL-12 p70) and IFN-γ in PBMCs or in whole blood. The increased levels of IL-12 observed when using compounds of the present invention results in much lower $EC_{50}$ values compared with other known p38 MAPK inhibitors. Increase in both IL-12 (IL-12 p70) and IFN-γ is observed in PBMCs or whole blood at concentrations of less than 300 nM, for example IL-12 p70 $EC_{50}$ levels of ≤1 nM and IFN-γ $EC_{50}$ of 1 nM are observed in PBMCs stimulated with LPS. For the p38 inhibitors PF-797804 (3-Bromo-4-[(2,4-difluorobenzyl)oxy]-1-[5-[(methylamino)carbonyl]-2-methylphenyl]-6-methylpyridin-2(1H)-one, 3-[3-Bromo-4-[(2,4-difluorophenyl)methoxy]-6-methyl-2-oxo-1(2H)-pyridinyl]-N,4-dimethyl-benzamide) and 6-Amino-5-(2,4-difluorobenzoyl)-1-[2,6-difluorophenyl]pyridin-2(1H)-one, for example, increases of IL12 are not observed below inhibitor concentrations of 300 nM.

The compounds of the invention are known to have activity as p38 MAPK inhibitors. P38 MAPK inhibitors can be useful in the treatment of certain cancers where p38 MAPK is implicated. However, the findings of the present inventors, namely that the compounds provide beneficial immunomodulation, leads to potential new applications for the compounds. In particular, the compounds are useful in the treatment of certain cell proliferative diseases, in particular cancers, where an immune response is beneficial. The compounds are therefore useful in the treatment of cancer by modulation of the immune system, in particular by increasing stimulation of IL-12, coupled with increased IFN-γ production.

The compound or composition used in the invention may, therefore, be a useful in the treatment of cancer by stimulation of IL-12 production, in particular by stimulation of IL-12 production and IFN-γ production.

Cancers that may be treated with the compound are in particular cancers in which the tumour associated macrophages and dendritic cells exhibit an IL-12$^{low}$ phenotype. As the skilled person will be aware, immune cell populations of dendritic cell, lymphocyte and macrophage can be characterized with immunohistochemistry (IHC) and tissue messenger RNA (mRNA) levels of Th1 cytokines interferon (IFN)-γ and its upstream inducer interleukin (IL)-12 can be quantified with real-time PCR (Cui et al, Cancer Immunol Immunother. 2007, 56(12), 1993-2001).

Examples of cancers which can be treated by increasing levels of IL-12 include head and neck cancer, melanoma, renal cancer, prostate cancer, breast cancer, bladder cancer, ovarian cancer, pancreatic cancer, acute myeloid cancer, cervical cancer, glioma, lung cancer, gastric cancer, hepatocellular carcinoma, colon cancer, mesothelioma, multiple myeloma, lymphoma, esophageal cancer and thyroid cancer. In one embodiment the cancers are ovarian cancer, breast cancer and lung cancer.

Preferably, the cancers which can be treated by increasing levels of IL-12 include head and neck cancer, prostate cancer, bladder cancer, acute myeloid cancer, cervical cancer, glioma, gastric cancer, hepatocellular carcinoma, mesothelioma, multiple myeloma, esophageal cancer or thyroid cancer. More preferably, the cancer which can be treated by increasing levels of IL-12 is cervical cancer.

In one embodiment the compounds are administered to a mammalian subject, in particular a human subject.

The present invention is further illustrated in the Examples which follow.

EXAMPLES

The ester compound used in the invention may be prepared according to the following Example.

Abbreviations

CDI=carbonyldiimidazole
DCM=dichloromethane
DMF=dimethylformamide
EtOAc=ethyl acetate
HCl=hydrochloric acid
LCMS=high performance liquid chromatography/mass spectrometry
MeOH=methanol
$MgSO_4$=magnesium sulphate
$Na_2CO_3$=sodium carbonate
$NaHCO_3$=sodium hydrogen carbonate
NMR=nuclear magnetic resonance
STAB=sodium triacetoxyborohydride
THF=tetrahydrofuran
g=gram(s)
mg=milligram(s)
mL=millilitre(s)
mmol=millimole(s)

Commercially available reagents and solvents (HPLC grade) were used without further purification. Solvents were removed using a Buchi rotary evaporator. Microwave irradiation was carried out using a Biotage Initiator™ Eight microwave synthesiser. Purification of compounds by flash chromatography column was performed using silica gel, particle size 40-63 μm (230-400 mesh) obtained from Fluorochem.

$^1$H NMR spectra were recorded on a Bruker 300 MHz AV spectrometer in deuterated solvents. Chemical shifts (d) are in parts per million. Thin-layer chromatography (TLC) analysis was performed with Kieselgel 60 F$_{254}$ (Merck) plates and visualized using UV light.

Analytical HPLC/MS was performed on an Agilent HP1100 LC system using reverse phase Luna C18 columns (3 mm, 50×4.6 mm), gradient 5-95% B (A=water/0.1% Formic acid, B=acetonitrile/0.1% Formic acid) over 2.25 min, flow=2.25 mL/min. UV spectra were recorded at 220 and 254 nm using a G1315B DAD detector. Mass spectra were obtained over the range m/z 150 to 800 on a LC/MSD SL G1956B detector. Data were integrated and reported using ChemStation and ChemStation Data Browser software.

INTERMEDIATES

Intermediate 1: 4-Chlorophenyl 3-(2,4-difluorophenyl)-3-oxopropanimidothioate hydrochloride

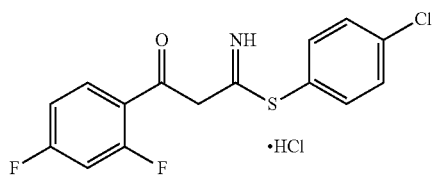 [SMILES: N=C(CC(=O)c1ccc(F)cc1F)Sc1ccc(Cl)cc1 ; Cl]

Intermediate 1 can be prepared using experimental procedures described in WO 2003076405.

Intermediate 2: 2-(4-Amino-3,5-difluorophenyl)ethanol

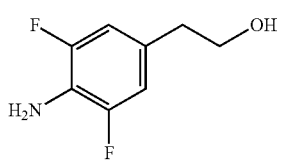

Intermediate 2 was synthesised using the route shown in Scheme 1 below.

Scheme 1

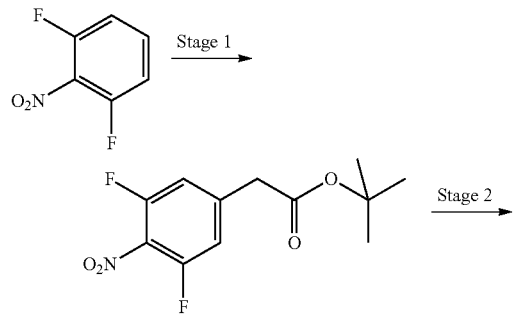

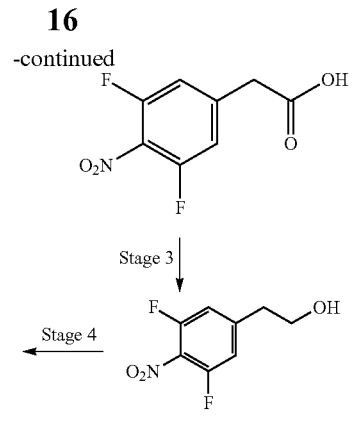

Intermediate 2

Stage 1—tert-Butyl (3,5-difluoro-4-nitrophenyl)acetate

A solution of difluoronitrobenzene (24.96 g, 157 mmol) and tert-butyl chloroacetate (38.0 mL, 267 mmol) in anhydrous DMF (200 mL) was added dropwise over one hour to a cold (−35° C.) suspension of potassium tert-butoxide (61.61 g, 549 mmol) in anhydrous DMF (200 mL) under nitrogen. The reaction mixture was stirred at −35° C. for 1.5 hours, quenched with 2N HCl (240 mL) and extracted with heptanes (4×200 mL). The combined organic extracts were washed with water (3×200 mL), brine (200 mL), dried (MgSO$_4$), filtered and concentrated under reduced pressure to leave a yellow oil. Purification by column chromatography (10% EtOAc in heptanes) afforded a yellow oil (37.64 g). Another two batches (10.00 g and 23.54 g of difluoronitrobenzene) afforded 14.30 g and 31.39 g of product respectively. $^1$H NMR's of all three batches showed a mixture of desired compound and small amounts of unidentified impurities. The 3 batches were combined and used in the next stage without further purification.

$^1$H NMR (300 MHz, CDCl$_3$) 7.05 (2H, d, J=8.5 Hz), 3.56 (2H, s), 1.46 (9H, s).

Stage 2—(3,5-Difluoro-4-nitrophenyl)acetic acid

Trifluoroacetic acid (150 mL) was added dropwise over 20 minutes to a cold (0° C.) solution of tert-butyl (3,5-difluoro-4-nitrophenyl)acetate (83.33 g, 305 mmol) in DCM (300 mL). On completion of the addition, the reaction mixture was allowed to warm to room temperature and stirred for 3 hours. The reaction mixture was concentrated under reduced pressure to leave a sticky brown solid. Trituration with heptanes afforded the title compound as a yellow solid (53.29 g, 67% yield over two steps).

$^1$H NMR (300 MHz, CDCl$_3$) 7.08 (2H, d, J=8.5 Hz), 3.74 (2H, s), —CO$_2$H not visible.

Stage 3—2-(3,5-Difluoro-4-nitrophenyl)ethanol

Borane-dimethyl sulfide complex (35 mL, 368 mmol) was added dropwise over 20 minutes to a cold (0° C.) solution of (3,5-difluoro-4-nitrophenyl)acetic acid (53.29 g, 245 mmol)

in anhydrous THF (500 mL) under nitrogen. Upon completion of the addition, the reaction mixture was allowed to warm to room temperature, stirred for 16 hours, cooled to 0° C., carefully quenched with MeOH (300 mL) and concentrated under reduced pressure to leave a brown oil. Purification by dry flash chromatography (60-80% EtOAc in heptanes) afforded the title compound as an orange oil (38.90 g, 78% yield).

$^1$H NMR (300 MHz, CDCl$_3$) 7.01 (2H, d, J=8.7 Hz), 3.93 (2H, t, J=6.2 Hz), 2.92 (2H, t, J=6.2 Hz), 2.34 (1H, br s).

Stage 4—2-(4-Amino-3,5-difluorophenyl)ethanol 2-(3,5-Difluoro-4-nitrophenyl)ethanol (38.90 g, 191 mmol) was dissolved in EtOAc (250 mL). The reaction vessel was evacuated and filled with nitrogen three times. Palladium on carbon (10 wt %, 4.00 g) was added and the vessel was evacuated and filled with nitrogen three times. Finally, the vessel was evacuated and filled with hydrogen and fitted with a balloon containing hydrogen. After, stirring at room temperature under hydrogen for 15 hours, the hydrogen balloon was refilled and the mixture stirred for an additional 25 hours. The reaction mixture was filtered through Celite® and the filtrate was concentrated under reduced pressure to leave a brown oil. Purification by dry flash chromatography (50% EtOAc in heptanes) afforded the title compound as a beige solid (20.70 g, 62% yield).

$^1$H NMR (300 MHz, CDCl$_3$) 6.73-6.70 (2H, m), 3.81 (2H, t, J=6.4 Hz), 2.75 (2H, t, J=6.4 Hz), —OH and —NH$_2$ not visible.

Example 1: tert-Butyl N-(2-{4-[6-amino-5-(2,4-difluorobenzoyl)-2-oxopyridin-1(2H)-yl]-3,5-difluorophenyl}ethyl)-L-alaninate

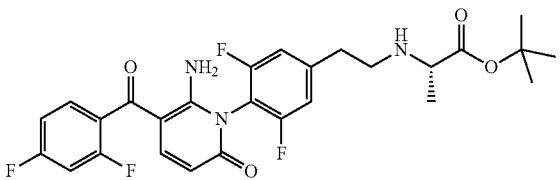 [SMILES: C[C@H](NCCc1cc(F)c(-n2c(N)c(C(=O)c3ccc(F)cc3F)ccc2=O)c(F)c1)C(=O)OC(C)(C)C]

Example 1 was synthesised using the route shown in Scheme 2 below.

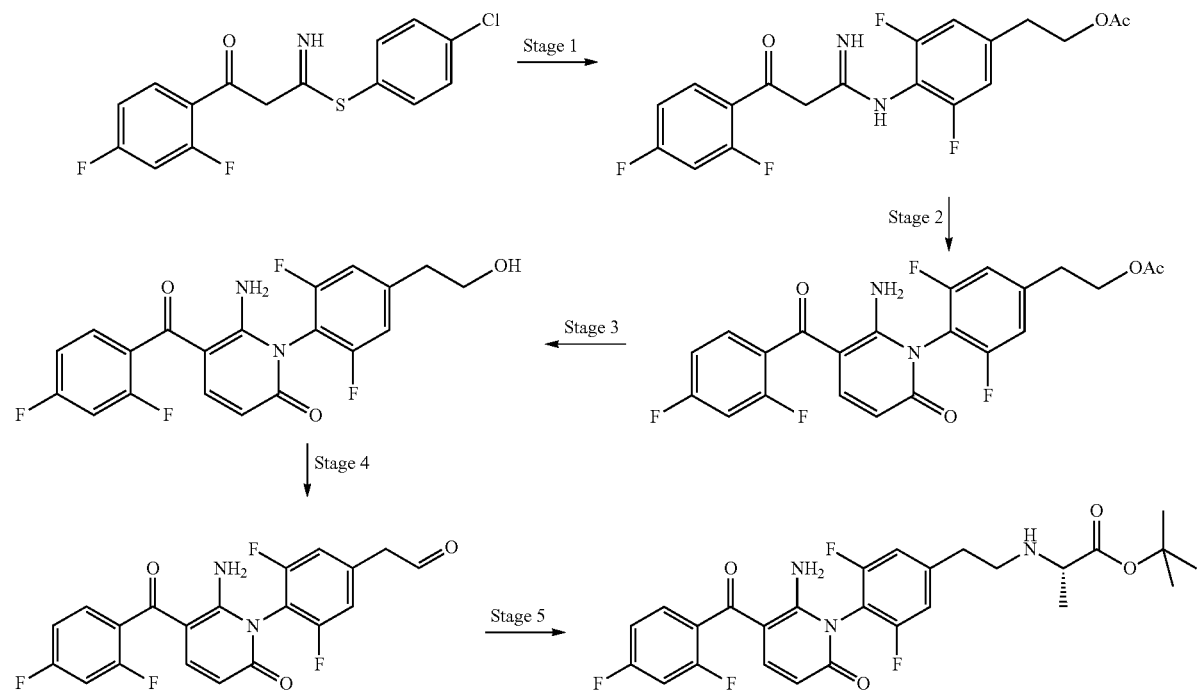

Stage 1—2-(4-{[3-(2,4-Difluorophenyl)-3-oxopropanimidoyl]amino}-3,5-difluorophenyl)ethyl acetate 2-(4-Amino-3,5-difluorophenyl)ethanol (20.71 g, 120 mmol) was added to a solution of 4-chlorophenyl 3-(2,4-difluorophenyl)-3-oxopropanimidothioate hydrochloride (41.26 g, 114 mmol) in glacial acetic acid (400 mL). The reaction mixture was stirred at 80° C. for 2.5 hours and acetic anhydride (21 mL, 228 mmol) was added. After an additional 45 minutes at 80° C., the reaction mixture was allowed to cool to room temperature and concentrated under reduced pressure to leave a brown oil. Trituration with EtOAc afforded a beige solid, which was washed with diethyl ether. The solid was taken up in a saturated aqueous solution of NaHCO$_3$ and vigorously stirred for 30 minutes. A solid was collected by filtration, washed with water and allowed to dry under reduced pressure to afford the title compound as a beige solid (23.36 g, 52% yield).

LCMS: m/z 397 [M+H]$^+$.

Stage 2—2-{4-[6-Amino-5-(2,4-difluorobenzoyl)-2-oxopyridin-1(2H)-yl]-3,5-difluorophenyl}ethyl acetate Propiolic acid (5.4 mL, 88 mmol) was added dropwise over 5 minutes to a cold (0° C.) solution of CDI (14.27 g, 88 mmol) in anhydrous THF (400 mL) under nitrogen. After completion of the addition, the reaction mixture was allowed to warm to room temperature and stirred for one hour. A solution of 2-(4-{[3-(2,4-difluorophenyl)-3-oxopropanimidoyl]amino}-3,5-difluoro-phenyl)ethyl acetate (23.26 g, 59 mmol) in anhydrous THF (200 mL) was added and the reaction mixture was stirred at reflux for 6.5 hours. The reaction mixture was allowed to cool to room temperature and left standing for 16.5 hours. Propiolic acid (5.4 mL, 88 mL), CDI (14.27 g, 88 mmol) and THF (200 mL) were treated as described above and added to the reaction mixture, which was subsequently stirred at reflux for an additional 6 hours. The reaction mixture was then allowed to cool to room temperature and concentrated under reduced pressure to leave a brown oil. Purification by dry flash chromatography (5% MeOH in DCM) gave a dark brown solid, which was further purified by trituration with EtOAc to afford the title compound as a yellow solid (7.45 g, 28% yield).

LCMS: m/z 449 [M+H]$^+$ and 471 [M+Na]$^+$.

Stage 3—6-Amino-5-(2,4-difluorobenzoyl)-1-[2,6-difluoro-4-(2-hydroxyethyl)phenyl]pyridin-2(1H)-one 2-{4-[6-Amino-5-(2,4-difluorobenzoyl)-2-oxopyridin-1 (2H)-yl]-3,5-difluorophenyl}ethyl acetate (7.45 g, 17 mmol) was suspended in 6N HCl (80 mL) and the reaction mixture was refluxed for 21.5 hours. A solid was collected by filtration, taken up in a saturated aqueous solution of NaHCO$_3$ (200 mL) and vigorously stirred for 30 minutes. A solid was collected by filtration, washed with water and dried in a vacuum oven (40° C.) to afford the title compound as a beige solid.

LCMS: m/z 407 [M+H]$^+$ and 429 [M+Na]$^+$.

$^1$H NMR (300 MHz, DMSO-d$_6$) 7.57 (1H, td, J=6.6, 8.3 Hz), 7.41 (1H, td, J=2.4, 9.7 Hz), 7.37-7.29 (3H, m), 7.23 (1H, td, J=2.3, 8.5 Hz), 5.74 (1H, d, J=9.8 Hz), 4.78 (1H, t, J=5.1 Hz), 3.76-3.70 (2H, m), 2.86 (2H, t, J=6.7 Hz), —NH$_2$ not visible

Stage 4—{4-[6-Amino-5-(2,4-difluorobenzoyl)-2-oxopyridin-1(2H)-yl]-3,5-difluorophenyl}-acetaldehyde Dess-Martin periodinane (1.03 g, 2.4 mmol) was added to a suspension of 6-amino-5-(2,4-difluorobenzoyl)-1-[2,6-difluoro-4-(2-hydroxyethyl)phenyl]pyridin-2(1H)-one (823 mg, 2.0 mmol) in DCM (20 mL). The reaction mixture was stirred at room temperature for 2 hours, quenched with a saturated aqueous solution of NaHCO$_3$ (10 mL) and a saturated aqueous solution of sodium thiosulfate (10 mL) and vigorously stirred for 30 minutes. The aqueous layer was separated and further extracted with DCM (2×20 mL). The combined organic extracts were dried (MgSO$_4$), filtered and concentrated under reduced pressure to afford the title compound as a pale brown solid (819 mg). This was used without further purification in the next stage.

Stage 5—tert-Butyl N-(2-{4-[6-amino-5-(2,4-difluorobenzoyl)-2-oxopyridin-1(2H)-yl]-3,5-difluorophenyl}ethyl)-L-alaninate tert-Butyl L-alaninate hydrochloride (552 mg, 3.0 mmol) and STAB (1.29 g, 6.1 mmol) were added to a solution of {4-[6-amino-5-(2,4-difluorobenzoyl)-2-oxopyridin-1(2H)-yl]-3,5-difluorophenyl}-acetaldehyde (819 mg, 2.0 mmol). The reaction mixture was stirred at room temperature for 3.5 hours, quenched with a saturated aqueous solution of Na$_2$CO$_3$ (20 mL) and vigorously stirred for 20 minutes. The aqueous layer was separated and further extracted with EtOAc (2×20 mL). The combined organic extracts were washed with brine (20 mL), dried (MgSO$_4$), filtered and concentrated under reduced pressure to leave a yellow oil. Purification by column chromatography (5% MeOH in DCM) afforded the title compound as a pale yellow solid (492 mg, 78% yield over two steps).

LCMS: purity 98%, m/z 534 [M+H]$^+$.

$^1$H NMR (300 MHz, DMSO-d$_6$) 7.58 (1H, td, J=6.8, 8.3 Hz), 7.41 (1H, td, J=2.3, 9.8 Hz), 7.37-7.30 (3H, m), 7.23 (1H, td, J=2.3, 8.5 Hz), 5.74 (1H, d, J=9.8 Hz), 3.20 (1H, d, J=7.0 Hz), 2.89-2.70 (4H, m), 1.42 (9H, s), 1.16 (3H, d, J=7.0 Hz), —NH$_2$ and —NH— not visible Measurement of Biological Activities

Example 2

Human PBMCs from six healthy donors were isolated from whole blood. PBMCs were resuspended in RPMI-10 at 1×10$^6$/mL and plated at a density of 2×10$^5$ per well (200 μL) in 96-well round bottom culture plates. Treatments or reference controls at different concentrations were prepared in DMSO according to client/supplier instruction and added directly to wells at a final volume of 0.2 μL per well (1:1000). After 2 hours, LPS was added to the culture (1 μg/mL final, 10 μL per well). Cells were cultured for 72 hrs at 37° C. and 5% CO$_2$. Cell-free supernatants were collected at the end of culture period, transferred to new 96-well plates and frozen at −80° C. prior to assessment of IFN-γ, IL-10, IL-12p70 and TNF-α by ELISA and multiplex immunoassay.

Study Design
Groups Included:
Unstimulated PBMCs
Stimulated PBMCs+Vehicle (DMSO)
Stimulated PBMCs+6-Amino-5-(2,4-difluorobenzoyl)-1-[2,6-difluorophenyl]pyridin-2(1H)-one at test concentartions 0 nM, 100 nM, 10 nM, 1 nM, 0.1 nM, 0.01 nM
Stimulated PBMCs+tert-butyl N-[2-{4-[6-amino-5-(2,4-difluorobenzoyl)-2-oxopyridin-1(2H)-yl]-3,5-difluorophenyl}ethyl)-L-alaninate at test concentrations 1000 nM, 100 nM, 10 nM, 1 nM, 0.1 nM, 0.01 nM
Stimulated PBMCs+PH797804 at test concentrations 10 nM, 100 nM, 10 nM, 1 nM, 0.1 nM, 0.01 nM
Cultures were performed in triplicate to provide technical replicates and PBMCs from six healthy donors were included to provide biological replication.

Study Formulations
Test and Reference Substance Storage
The test substances were stored at room temperature for lyophilised and at −20° C. once reconstituted. The reference substance was stored according to the instructions provided by the supplier −20° C. for lyophilised and −80° C. once reconstituted.

Test and Reference Substance Formulation
All test and reference substances were formulated at 10 mM stock concentration in anhydrous DMSO, filtered and frozen in aliquots. Immediately prior to addition to assay, stock solutions were diluted in DMSO to prepare solutions at 1000 times the final required concentration. All final formulations were freshly prepared and kept sterile and light protected prior to the addition in cultures.

Data Processing and Statistical Analysis

ELISA plates were read at 450 nm using an Infinite F50 (Tecan) absorbance reader and Magellan™ reader control and data analysis software. Multiplex immunoassays were read using a Luminex MAGPIX multiplexing system and ProcartaPlex Analyst 1.0 software. Graphs were prepared using Graphpad Prism (v6.0). Data were normalised to mean of respective vehicle control group (100%) within each biological replicate to account for donor variation.

Statistical analyses were made between tert-butyl N-[2-{4-[6-amino-5-(2,4-difluorobenzoyl)-2-oxopyridin-1(2H)-yl]-3,5-difluorophenyl}ethyl)-L-alaninate and 6-Amino-5-(2,4-difluorobenzoyl)-1-[2,6-difluorophenyl]pyridin-2(1H)-one using two-way ANOVA followed by Dunnett's multiple comparison test. Statistical significance was assumed when P<0.05.

The data in Table 2 demonstrate that tert-butyl N-[2-{4-[6-amino-5-(2,4-difluorobenzoyl)-2-oxopyridin-1(2H)-yl]-3,5-difluorophenyl}ethyl)-L-alaninate shows stimulation of IL-12 production from human monocytes in peripheral blood mononuclear cell (PBMC) samples with an EC50 value of <1 nM.

TABLE 2

| Compound | Inhibition of p38 MAPK $EC_{50}$ (nM) | Stimulation of IL-12p70 in PBMC's stimulated with LPS $EC_{50}$ (nM) |
| --- | --- | --- |
| tert-butyl N-[2-{4-[6-amino-5-(2,4-difluorobenzoyl)-2-oxopyridin-1(2H)-yl]-3,5-difluorophenyl}ethyl)-L-alaninate | 12 | <1 |
| 6-Amino-5-(2,4-difluorobenzoyl)-1-[2,6-difluorophenyl]pyridin-2(1H)-one | <1 | >300 |
| PH797804 | 1 | >300 |

The data in Table 3 demonstrate another unexpected result of hCE-1 mediated accumulation of the acid derived from tert-butyl N-[2-{4-[6-amino-5-(2,4-difluorobenzoyl)-2-oxopyridin-1(2H)-yl]-3,5-difluorophenyl}ethyl)-L-alaninate in the monocytes present in PBMC's in an increase in IFN-γ production at inhibitor concentrations with an EC50 value of 1 nM.

TABLE 3

| Compound | Inhibition of p38 MAPK $EC_{50}$ (nM) | Stimulation of INF-γ in PBMCs stimulated with LPS $EC_{50}$ (nM) |
| --- | --- | --- |
| tert-butyl N-[2-{4-[6-amino-5-(2,4-difluorobenzoyl)-2-oxopyridin-1(2H)-yl]-3,5-difluorophenyl}ethyl)-L-alaninate | 12 | 1 |
| 6-Amino-5-(2,4-difluorobenzoyl)-1-[2,6-difluorophenyl]pyridin-2(1H)-one | <1 | No stimulation observed at all concentrations up to and including 1000 nM |
| PH797804 | 1 | No stimulation observed at all concentrations up to and including 1000 nM |

These data demonstrate that tert-butyl N-[2-{4-[6-amino-5-(2,4-difluorobenzoyl)-2-oxopyridin-1(2H)-yl]-3,5-difluorophenyl}ethyl)-L-alaninate stimulates both IL-12 production and IFN-γ production, providing an unexpected benefit in immune rejection of tumours with advantage over other known p38 MAPK inhibitors.

TABLE 4

| Compound | Inhibition of p38 MAPK $EC_{50}$ (nM) | Inhibition of IL10 in PBMC's stimulated with LPS $IC_{50}$ (nM) |
| --- | --- | --- |
| tert-butyl N-[2-{4-[6-amino-5-(2,4-difluorobenzoyl)-2-oxopyridin-1(2H)-yl]-3,5-difluorophenyl}ethyl)-L-alaninate | 12 | <1 |
| 6-Amino-5-(2,4-difluorobenzoyl)-1-[2,6-difluorophenyl]pyridin-2(1H)-one | <1 | 10 |
| PH797804 | 1 | 10 |

These data demonstrate that tert-butyl N-[2-{4-[6-amino-5-(2,4-difluorobenzoyl)-2-oxopyridin-1(2H)-yl]-3,5-difluorophenyl}ethyl)-L-alaninate inhibits IL10 production at concentrations at least 10-fold lower than conventional p38 MAPK inhibitors such as 6-Amino-5-(2,4-difluorobenzoyl)-1-[2,6-difluorophenyl]pyridin-2(1H)-one and PH797804 which do not cause intracellular accumulation of p38MAPK inhibitor. The increase in IL10 inhibitory activity provided by tert-butyl N-[2-{4-[6-amino-5-(2,4-difluorobenzoyl)-2-oxopyridin-1(2H)-yl]-3,5-difluorophenyl}ethyl)-L-alaninate provides an unexpected benefit in immune rejection of tumours with advantage over other known p38 MAPK inhibitors given that it shows 10-fold less potent inhibitory activity against p38 MAPK than 6-Amino-5-(2,4-difluorobenzoyl)-1-[2,6-difluorophenyl]pyridin-2(1H)-one and PH797804.

The invention claimed is:

1. A method of stimulating IL-12 production and IFN-γ production in a subject, which method comprises administering to said subject an effective amount of a compound, which compound is selected from:
   tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof; and
   N-[2-{4-[6-amino-5-(2,4-difluorobenzoyl)-2-oxopyridin-1(2H)-yl]-3,5-difluorophenyl}ethyl)-L-alanine.

2. The method according to claim 1 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

3. The method according to claim 1, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

4. The method according to claim 1, wherein the method is a method of ameliorating or reducing cancer by stimulation of IL-12 production, wherein the cancer is a cancer characterized by macrophages and dendritic cells exhibiting an IL-12$^{low}$ phenotype.

5. The method according to claim 1, wherein the method is a method of ameliorating or reducing cancer and wherein the cancer is selected from head and neck cancer, prostate cancer, bladder cancer, acute myeloid cancer, cervical cancer, glioma, gastric cancer, hepatocellular carcinoma, mesothelioma, multiple myeloma, esophageal cancer, thyroid cancer, melanoma, breast cancer, colon cancer, pancreatic cancer, and renal cancer.

6. The method according to claim 1, which method comprising administering said compound to said subject in a composition comprising said compound together with one or more pharmaceutically acceptable carriers and/or excipients.

7. A method according to claim 6 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

8. The method according to claim 6, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

9. A method for ameliorating or reducing cell proliferative disease by stimulation of IL-12 production, which method comprises administering to said subject an effective amount of a compound,
which compound is selected from:
tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof; and
N-[2-{4-[6-amino-5-(2,4-difluorobenzoyl)-2-oxopyridin-1(2H)-yl]-3,5-difluorophenyl}ethyl)-L-alanine.

10. The method according to claim 9 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

11. The method according to claim 9, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

12. A method for ameliorating or reducing cancer by stimulation of IL-12 production, which method comprises administering to said subject an effective amount of a compound,
which compound is selected from:
tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof; and
N-[2-{4-[6-amino-5-(2,4-difluorobenzoyl)-2-oxopyridin-1(2H)-yl]-3,5-difluorophenyl}ethyl)-L-alanine,
wherein the cancer is selected from head and neck cancer, prostate cancer, bladder cancer, acute myeloid cancer, cervical cancer, glioma, gastric cancer, hepatocellular carcinoma, mesothelioma, multiple myeloma, esophageal cancer, thyroid cancer, melanoma, breast cancer, colon cancer, pancreatic cancer, and renal cancer.

13. The method according to claim 12, wherein the method is a method of ameliorating or reducing cancer and wherein the cancer is selected from head and neck cancer, prostate cancer, bladder cancer, acute myeloid cancer, cervical cancer, gastric cancer, mesothelioma, multiple myeloma, and esophageal cancer.

14. The method according to claim 13 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

15. The method according to claim 13, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

16. The method according to claim 9, which method comprising administering said compound to said subject in a composition comprising said compound together with one or more pharmaceutically acceptable carriers and/or excipients.

17. The method according to claim 16 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

18. The method according to claim 16, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

19. The method according to claim 12, which method comprising administering said compound to said subject in a composition comprising said compound together with one or more pharmaceutically acceptable carriers and/or excipients.

20. The method according to claim 19 wherein the compound is tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

21. The method according to claim 19, wherein the compound is the ethanesulphonate salt of tert-butyl N-[2-{4-[6-amino-5-(2,4-difluorobenzoyl)-2-oxopyridin-1(2H)-yl]-3,5-difluorophenyl}ethyl)-L-alaninate.

22. The method according to claim 5, wherein the cancer is selected from head and neck cancer, prostate cancer, bladder cancer, acute myeloid cancer, cervical cancer, gastric cancer, mesothelioma, multiple myeloma and esophageal cancer.

23. The method according to claim 5, wherein the cancer is selected from bladder cancer, hepatocellular carcinoma, melanoma, breast cancer, colon cancer, glioma, pancreatic cancer, cervical cancer, multiple myeloma, renal cancer, and gastric cancer.

24. The method according to claim 12, wherein the cancer is selected from bladder cancer, hepatocellular carcinoma, melanoma, breast cancer, colon cancer, glioma, pancreatic cancer, cervical cancer, multiple myeloma, renal cancer, and gastric cancer.

* * * * *